United States Patent [19]

Andersson et al.

[11] Patent Number: 5,441,976

[45] Date of Patent: Aug. 15, 1995

[54] PHARMACOLOGICAL USE OF CERTAIN CYSTINE DERIVATIVES

[75] Inventors: Carl-Magnus A. Andersson; Håkan S. A. Bergstrand; Anders R. Hallberg, all of Lund; Bengt O. Särnstrand, Bjärred; Anders P. S. Tunek, Malmö, all of Sweden

[73] Assignee: Aktiebolaget Astra, Sodertalje, Sweden

[21] Appl. No.: 949,648

[22] Filed: Dec. 4, 1992

[30] Foreign Application Priority Data

Jun. 8, 1990 [SE] Sweden .................. 9002067
Jun. 28, 1990 [SE] Sweden .................. 9002275

[51] Int. Cl.$^6$ .................. A61K 31/195; A61K 31/22; A61K 31/225; C07C 323/59
[52] U.S. Cl. .................. 514/410; 514/422; 514/423; 514/563
[58] Field of Search .............. 514/410, 422, 423, 563; 548/527, 537, 519

[56] References Cited

U.S. PATENT DOCUMENTS

| | | | |
|---|---|---|---|
| 3,878,305 | 4/1975 | Damico et al. | 426/104 |
| 3,952,115 | 4/1976 | Damico et al. | 426/590 |
| 4,708,965 | 11/1987 | Morgan | 514/563 |
| 4,724,239 | 2/1988 | Morgan | 514/563 |
| 4,827,016 | 5/1989 | Morgan | 560/16 |
| 5,254,579 | 10/1993 | Poli et al. | 514/422 |

FOREIGN PATENT DOCUMENTS

| | | |
|---|---|---|
| 0300100 | 1/1989 | European Pat. Off. . |
| 8205M | 10/1970 | France . |
| 2503151 | 10/1982 | France . |
| 2326444 | 12/1973 | Germany . |
| 2097256 | 11/1982 | United Kingdom . |

OTHER PUBLICATIONS

Martin, "N-Acyl- and N-Sulfonylcysteine Derivatives", Journal of Med. Chem., vol. 12, Sep. 1969, pp. 950-953.

Sjodin et al., "Metabolism of N-acetyl-L-cysteine . . . ", Biochemical Pharmacology, vol. 38, No. 22, 1989, pp. 3981-3985.

Schaad et al.: "Linear Regession Analysis of Inhibitory Potency of Organic . . . " Journal of Med. Chem. vol. 18 No. 4, 1975.

Kahns et al., "Prodrugs as drug delivery systems . . . ", International Journal of Pharmaceutics, vol. 62, 1990, pp. 193–205.

Bowman et al., "Reactions of Thiolate anions . . . ", Tetrahedron Letters, vol. 22, No. 16, 1981, pp. 1551-1554.

Kemp et al., "Templates for Intramolecular . . . ", J. Org. Chem., vol. 54, 1989, pp. 3853-3858.

Patent Abstracts of Japan, vol. 12, No. 47, C475, abstracts of JP 62-195356, publ 1987-08-28, Seiwa Kasei K.K.

*Primary Examiner*—Arthur C. Prescott
*Attorney, Agent, or Firm*—White & Case

[57] ABSTRACT

A pharmaceutical preparation and method for the treatment of diseases due to defects in the immune system using cystine derivatives.

14 Claims, No Drawings

PHARMACOLOGICAL USE OF CERTAIN CYSTINE DERIVATIVES

FIELD OF THE INVENTION

The present invention relates to a new medical use of N,N'-diacetylcystine, N,N'-dibutyrylcystine, N,N'-diisovalerylcystine, N,N',-dicaprylylcystine, N,N'-diacetylcystine dimethyl ester, N,N'-diacetylcystine diethyl ester and N,N'-diisovalerylcystine dimethyl ester in racemic forms or in the form of optical D or L isomers.

In particular the invention relates to the use of the abovementioned compounds for the preparation of medicaments with immunomodulating action, particularly immunostimulating action.

BACKGROUND OF THE INVENTION

N-Acetyl-L-cysteine is a compound widely used for treating chronic obstructive airway diseases/chronic bronchitis (for further references see Multicentre Study Group. Long-term oral acetylcysteine in chronic bronchitis. A double-blind controlled study. Eur. J. Respir. Dis. 1980, 61 (suppl. 111), 93–108; Bowman, G., Bäcker, U., Larsson, S., Melander, B., and Wåhlander, L. Oral acetylcysteine reduces exacerbation rate in chronic bronchitis. Report of a trial organized by the Swedish Society for Pulmonary Disease. Eur. J. Respir. Dis. 1983, 64, 405–415; and British Thoracic Society Research Committee. Oral N-acetylcysteine and exacerbation rates in patients with chronic bronchitis and severe airway obstruction. Thorax 1985, 40, 832–835). The mechanism of action of the compound is not disclosed; its effect has been attributed to mucolytic properties (see Multicentre Study Group. Long-term oral acetylcysteine in chronic bronchitis. A double-blind controlled study. Eur. J. Respir. Dis. 1980, 61 (suppl. 111), 93–108; Boman, G., Bäcker, U., Larsson, S., Melander, B., and Wåhlander, L. Oral acetylcysteine reduces exacerbation rate in chronic bronchitis. Report of a trial organized by the Swedish Society for Pulmonary Disease. Eur. J. Respir. Dis. 1983, 64, 405–415; and British Thoracic Society Research Committee. Oral N-acetylcysteine and exacerbation rates in patients with chronic bronchitis and severe airway obstruction. Thorax 1985, 40,832–835), antioxidant properties (see Aruoma, O.I., Halliwell, B., Hoey, B. M., and Butler, J. Free Radical Biol. Mad. 1989, 6, 593–597), and also immunomodulating properties (see Bergstrand, H., Björnson, A., Eklund, A., Hernbrand, R., Eklund, A., Larsson, K., Linden M., and Nilsson, A. Stimuli-induced superoxide radical generation in vitro by human alveolar macrophages from smokers: Modulation by N-Acetylcysteine treatment in vivo. J. Free Radicals Biol. & Med. 2, 1986, 119–127).

The present invention deals with the disulfide of N-acetylcysteine, that is N,N'-diacetylcystine (in the following referred to as DiNAC), i.e. the compound of the formula:

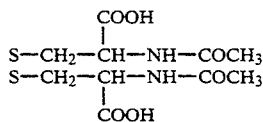

N,N'-dibutyrylcystine (in the following referred to as diBUT), i.e. the compound of the formula:

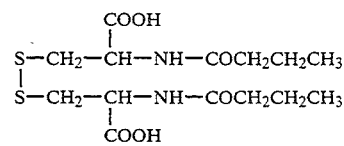

N,N'-diisovalerylcystine (in the following referred to as diBUT), i.e. the compound of the formula:

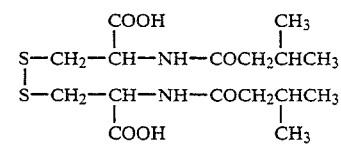

N,N'-dicaprylylcystine (in the following referred to as diCAP), i.e. the compound of the formula

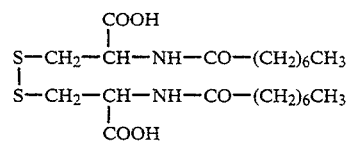

N,N'-diacetylcystine dimethyl ester ( in the following referred to as diMeNAC), i.e. the compound of the formula:

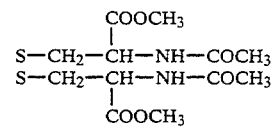

N,N'-diacetylcystine diethyl ester (in the following referred to as diEtNAC), i.e. the compound of the formula:

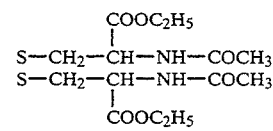

and N,N'-diisovalerylcystine dimethyl ester (in the following referred to as diMeVAL), i.e. the compound of the formula:

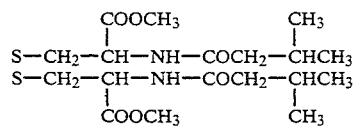

The invention deals with the above mentioned compounds in racemic form as well as the isomeric D and L forms of the compounds. Of particular interest are the compounds having the L configuration, particularly interesting is N,N'-diacetyl-L-cystine.

The invention also deals with the compounds in the form of their physiologically acceptable salts such as the salts of sodium, potassium, ammonium, calcium or magnesium. Also included are salts of the compounds dINAC, diBUT, diVAL and diCAP with pharmaceutically acceptable organic bases.

The above mentioned compounds have previously been described in the patent literature as well as in the scientific literature. DiNAC in the following publications: U.S. Pat. No. 4,827,016; EP 300100; U.S. Pat. No. 4,724,239; U.S. Pat. No. 4,708,965; DE 2326444; Wilson, I. D., and Nicholson, J. K. Analysis of thiols and disulfides in Sulphur-containing drugs and related organic compounds. Chemistry, Biochemistry an Toxicology (ed L. A. Damani) Vol. 2A. Analytical, biochemical and toxicological aspects of sulphur xenobiochemistry. Ellis Horwood Series in Biochemical Pharmacology (Halstred Press: a division of John Wiley & Sons) Chichester 1989, p. 45; and Sjödin K., Nilsson E., Hallberg, A., and Tunek, A. Metabolism of N-Acetyl-L-cysteine. Some structural reguirements for the deacetylation and consequences for the oral biovailability. Biochem. Pharmacol. 1989, 38, 3981-3985). In U.S. Pat. No. 4,827,016 the compound is claimed to be effective for topical treatment of dermal inflammations which are induced and propagated by leukotrienes.

The remaining compounds have also been described in the literature. (See for instance, for diMeNAC: Bowman, W. R. Richardson, G. D. Tetrahedron Lett. 1981, 22, 1551–1554; for diEtNAC: Damico, R. A. Boggs, R. W. U.S. Pat. No. 3,952,115 (1976); for diVAL, diMeVAL: Martin, T. A. J. Med. Chem 1969, 12, 950–953), for diCAP: FR 8205 M, for diBUT: FR 2503151).

Nothing is reported or generally known concerning the pharmacological and/or therapeutic properties of these compounds with respect to immunological systems or inflammatory diseases of the lung such as chronic bronchitis.

DISCLOSURE OF THE INVENTION

It has unexpectedly been found that the hereinbefore mentioned compounds diNAC, diBUT, diVAL, diCAP, diMeNAC, diEtNAC and diMeVAL in an experimental animal model for assessing a T-cell reactivity in vivo, i.e. the delayed type hypersensitivity (DTH) reaction in the mouse ear, are highly potent and efficient immunostimulating agents, some being in the order of 100-1000 times more effective than the thiol NAC. Thus, in this model the compounds are highly effective immunostimulators with a potency and efficacy superior or equal to known immunostimulants such as diethyl dithiocarbamate (DTC) or hydroxyethyl disulfide (HEDS; see St Georgiev, V. New synthetic immunomodulating agents. Trends in Pharmacological Science 1988, 446–451).

Therefore, the compounds DiNAC, diBUT, diVAL, diCAP, diMeNAC, diEtNAC, diMeVAL and their D and L optical isomers may be used for treatment of diseases where a defect in the immune system and/or an ineffective host defence is at hand or can be suspected.

Examples of such diseases are chronic bronchitis and other inflammatory diseases of the airways such as asthma and rhinitis but also certain forms of autoimmune diseases like diabetes and rheumatoid arthritis and/or various malignant diseases. HIV infection or AIDS may be treated with the compounds. Also atherosclerotic disease maybe treated with the compounds.

Effective amounts of the compounds diNAC, diBUT, diVAL, diCAP, diMeNAC, diEtNAC, diMeVAL and their D and L optical isomers for use in the treatment of the above mentioned diseases are in the range 0.5-500 daily dose.

Synthesis of compounds

The compounds diNAC, diBUT, diVAL and diCAP may be prepared, for example, from L-cystine via acylation (see U.S. Pat. No. 4,827,016; EP 300100; U.S. Pat. No. 4,724,239; U.S. Pat. No. 4,708,965; DE 2,326,444; Marshall, R., Winitz, M., Birnbaum, S. M. and Greenstein, J. P. J. Am. Chem. Soc. 1957, 79, 4538-4544; and Cecil, R. McPhee, J. B. Biochem. J. 1957, 66, 538-543) or through oxidative dimerization of the appropriate acylcysteines (see Snow, J. T., Finley, J. W. Friedman, M. Biochem. Biophys. Res. Commun. 1975, 64, 441-447).

The esters diMeNAt, diEtNAC and diMeVAL may be synthesized analogously, i.e. by acylation of the cystine methyl or ethyl esters as appropriate or by oxidative dimerisation of the respective N-acetyl cystine methyl or ethyl esters or N-isovalerylcysteine methyl ester. For examples of preparations, see Bonnett, R., Nicolaidow, P. J. Chem. Soc. Perkin Trans. I 1979, 1069-1077. Schaad, L. J., Werner, R. M., Dillon, L., Field, L., Tate, C. E. J. Med. Chem. 1975, 18, 344-351, and Martin, T. A. J. Med. Chem. 1969, 12,950-953.

Effects of compounds in a model of delayed type hypersensitivity in the mouse

The property of the compounds diNAC, diBUT, diVAL, diCAP, diMeNAC, diEtNAC and diMeVAL to stimulate immune responses is illustrated by their efficacy in a model of the delayed type hypersensitivity (DTH) reaction in the mouse.

Both male and female Balb/c mice obtained from Bomholtsgaard (Denmark) and Charlie Rivers (England), were used at the weight of 18-20 gram. 4-ethoxymethylene-2-phenyloxazolone (OXA) was purchased free BDH (England) and served as an antigen in this test.

The mice were sensitized, Day 0, by epicutaneous application of 150 $\mu$l absolute ethanol-acetone (3:1) solution containing 3% OXA on the shaved thorax end abdomen. Treatment with the L-form of diNAC, diMeNAC, diEtNAC, diMeVAL, or vehicle (phosphate buffer, pH 7.0) was initiated by oral feeding immediately after sensitization and continued once daily to Day 6. Seven days (Day 6) after the sensitization both ears of all mice were challenged on both sides by topical application of 20 $\mu$l 1% OXA dissolved in peanut oil. Ear thickness was measured prior to and 24 or 48 hours after challenge using an Oditest spring calliper. Challenges and measurements were performed under light pentobarbital anasthesia. The intensity of the DTH reactions was expressed according to the formula: $T_{t24/48} - T_{t0}$ $\mu$m units, where t0, t24 and t48 represent the ear thickness before and 24 or 48 hours after challenge, respectively, in an individual test (T). The results were expressed as the mean $\pm$S.E.M. The level of significance between means of the groups was obtained by Student's two-tailed t-test. Tables 1 and 2 show the results from 24 and 48 hours measurements, respectively, from a representative experiment with the L-form of diNAC. The results show that L-diNAC, after oral administration, caused a significant increase of the ear thickness in a concentration-response manner.

TABLE 1

| Ear thickness 24 hours after challenge of animals treated with the indicated doses of L-diNAC or vehicle. | | | | |
|---|---|---|---|---|
| Conc. $\mu$mol/kg | N | Diff. $T_{t24}-T_{t0}$ | S.E.M. | Sign. |
| Buffer | 13 | 7.85 | 0.32 | |

TABLE 1-continued

Ear thickness 24 hours after challenge of animals treated with the indicated doses of L-diNAC or vehicle.

| Conc. µmol/kg | N | Diff. $T_{t24}-T_{t0}$ | S.E.M. | Sign. |
|---|---|---|---|---|
| NaCl | 10 | 7.90 | 0.30 | n.s. |
| 0.03 | 10 | 13.75 | 0.47 | *** |
| 0.30 | 10 | 15.70 | 0.48 | *** |
| 3.0 | 10 | 18.30 | 1.02 | *** |
| 30.0 | 15 | 20.67 | 0.67 | *** |

***: $p < 0.001$

TABLE 2

Ear thickness 48 hours after challenge of animals treated with the indicated doses of L-diNAC or vehicle.

| Conc. µmol/kg | N | Diff. $T_{t48}-T_{t0}$ | S.E.M. | Sign. |
|---|---|---|---|---|
| Buffer | 14 | 9.64 | 0.35 | |
| NaCl | 10 | 9.85 | 0.54 | n.s. |
| 0.03 | 10 | 11.65 | 0.27 | *** |
| 0.30 | 10 | 12.65 | 0.48 | *** |
| 3.0 | 10 | 14.95 | 0.55 | *** |
| 30.0 | 15 | 13.63 | 0.30 | *** |

***: $p < 0.001$

Table 3 gives the correponding figures for ear thickness 24 and 48 hours after challenge of animals treated with diMeNAC and diEtNAC.

TABLE 3

Ear thickness 24 and 48 hours after challenge of animals treated with the L-forms of diMeNAC and diEtNAC.

| | Conc µmol/kg | N | Diff $T_{t24}-T_{t0}$ | S.E.M. | Sign. |
|---|---|---|---|---|---|
| | | | 24 h | | |
| Buffer | | 10 | 8.70 | 0.34 | — |
| diMeNAC | 0.03 | 10 | 18.00 | 0.84 | *** |
| | 3.0 | 10 | 12.55 | 0.88 | ** |
| diEtNAC | 0.03 | 10 | 11.75 | 0.62 | *** |
| | 3.0 | 10 | 13.05 | 0.59 | *** |
| | | | 48 h | | |
| diMeNAC | 0.03 | 10 | 12.85 | 0.67 | ** |
| | 3.0 | 10 | 13.35 | 0.67 | *** |
| diEtNAC | 0.03 | 10 | 13.15 | 0.53 | *** |
| | 3.0 | 10 | 13.20 | 0.66 | *** |

**: $p < 0.01$
***: $p < 0.001$

Pharmaceutical formulations

The described active substances can be included in different dosage forms e.g. tablets, coated tablets, gelatin capsules, solutions and aerosols.

For the preparation of tablets, coated tablets and gelatin capsules the active substances can be combined with pharmaceutically acceptable materials, e.g. lactose, starch, dicalcium phosphate, microcrystalline cellulose, polyvinylpyrrolidone, gelatin, cellulose derivatives, colloidal silicone dioxide, talc and stearic acid or its salts.

For the preparation of oral solutions suitable excipients are water, saccharose, glucose, sorbitol, fructose and xylitol.

The dosage forms can besides mentioned excipients contain preservatives, stabilizers, viscosity regulating agents, emulsifiers, sweetening agents, colouring agents, flavouring agents, tonicity regulating agents, buffers or antioxidants. They can also contain other therapeutically valuable substances.

EXAMPLE 1

Tablet containing 10 mg of active substance per tablet:

| Active substance | 10 mg |
|---|---|
| Lactose | 100 mg |
| Potato starch | 50 mg |
| Polyvinylpyrrolidone | 5 mg |
| Microcrystalline cellulose | 15 mg |
| Magnesium stearate | 1 mg |

EXAMPLE 2

Direct compression tablet containing 5 mg of active substance per tablet:

| Active substance | 5 mg |
|---|---|
| Lactose, anhydrous | 150 mg |
| Microcrystalline cellulose | 50 mg |
| Colloidal silicon dioxide | 1 mg |
| Magnesium stearate | 2 mg |

If desired, the obtained tablets can be film coated with e.g. hydroxypropyl methylcellulose, hydroxypropyl cellulose or dimethylaminoethyl methacrylate methacrylic acid ester copolymer.

EXAMPLE 3

Solution for injection containing active substance 1 mg/ml

| Active substance | 1.0 mg |
|---|---|
| Sodium chloride | 8.8 mg |
| Water for injection to | 1 ml |

EXAMPLE 4

Oral solution containing active substance 1 mg/ml

| Active substance | 1.0 mg |
|---|---|
| Sorbitol | 150 mg |
| Glycerin | 100 mg |
| Disodium edetate | 0.5 mg |
| Preservative | q.s. |
| Flavour | q.s. |
| Water, purified to | 1 ml |

EXAMPLE 5

Powder aerosol giving 1 mg per dose

The micronized active substance can be filled into a powder inhaler device e.g. Turbuhaler® giving 1 mg/dose.

We claim:

1. A pharmaceutical preparation for the treatment of diseases wherein an immunostimulating substance is effective, comprising as active ingredient a compound selected from the group consisting of racemic N,N'-dibutyrylcystine, N,N'-diisovalerylcystine, N,N'-dicaprylylcystine, N,N'-diacetylcystine dimethyl ester, N,N'-diacetylcystine diethyl ester, the D and L optical isomers thereof and physiologically acceptable salts thereof in a pharmaceutically acceptable carrier.

2. A method for the treatment of diseases resulting from a defect in the immune system in mammals wherein a daily dosage range of 0.5 mg to 500 mg of an active compound is administered internally to a host in need of such treatment, said active compound selected from the group consisting of racemic N,N'-diacetylcystine, N,N'-dibutyrylcystine, N,N'-diisovalerylcystine, N,N'-dicaprylylcystine, N,N'-diacetylcystine dimethyl ester, N,N'-diacetylcystine diethyl ester, N,N'-diisovalerylcystine dimethyl ester, the D and L optical isomers thereof and physiologically acceptable salts thereof, optionally together with a pharmaceutically acceptable carrier.

3. A method for stimulating the immune system of a mammal, which comprises internally administering to a host in need of such stimulation a daily dosage range of 0.5 mg to 500 mg of an active compound selected from the group consisting of racemic N,N'-diacetylcystine, N,N'-dibutyrylcystine, N,N'-diisovalerylcystine, N,N'-dicaprylylcystine, N,N'-diacetylcystine dimethyl ester, N,N'-diacetylcystine diethyl ester, N,N'-diisovaleryl-cystine dimethyl ester, the D and L optical isomers thereof and physiologically acceptable salts thereof, optionally together with a pharmaceutically acceptable carrier.

4. The pharmaceutical preparation according to claim 1, wherein the active ingredient is an L optical isomer.

5. The method according to claim 2 or 3 wherein the active compound is an L optical isomer.

6. The method according to claim 5 wherein the active compound is N,N'-diacetyl-L-cystine.

7. The method according to claim 2 wherein the disease is chronic bronchitis.

8. The method according to claim 2 wherein the disease is asthma.

9. The method according to claim 2 wherein the disease is rhinitis.

10. The method according to claim 2 wherein the disease is rheumatoid arthritis.

11. The method according to claim 2 wherein the disease is AIDS or a related HIV infection.

12. The method according to claim 2 wherein the disease is atherosclerosis.

13. The method according to claim 2 wherein the disease is diabetes.

14. The method according to claim 2 or 3, wherein the daily dosage of the active compound ranges from 5 mg to 50 mg.

* * * * *